(12) United States Patent
Okolo (10) Patent No.: US 10,647,632 B2
(45) Date of Patent: May 12, 2020

(54) PROCESS FOR PRODUCING CUMENE AND/OR ETHYLBENZENE FROM A MIXED HYDROCARBON FEEDSTREAM

(71) Applicant: SABIC Global Technologies B.V., Bergen op Zoom (NL)

(72) Inventor: Christian Okolo, Sittard (NL)

(73) Assignee: SABIC GLOBAL TECHNOLOGIES B.V., Bergen op Zoom (NL)

(*) Notice: Subject to any disclaimer, the term of this patent is extended or adjusted under 35 U.S.C. 154(b) by 18 days.

(21) Appl. No.: 15/740,125

(22) PCT Filed: Jun. 23, 2016

(86) PCT No.: PCT/EP2016/064571
§ 371 (c)(1),
(2) Date: Dec. 27, 2017

(87) PCT Pub. No.: WO2017/001284
PCT Pub. Date: Jan. 5, 2017

(65) Prior Publication Data
US 2018/0194702 A1   Jul. 12, 2018

(30) Foreign Application Priority Data
Jun. 29, 2015 (EP) .................................. 15174335

(51) Int. Cl.
*C07C 2/66* (2006.01)
*C07C 5/41* (2006.01)
(Continued)

(52) U.S. Cl.
CPC ............... *C07C 2/66* (2013.01); *C07C 5/415* (2013.01); *C07C 5/417* (2013.01); *C07C 15/04* (2013.01);
(Continued)

(58) Field of Classification Search
CPC .. C07C 2/66; C07C 5/393; C07C 5/41; C07C 5/415; C07C 5/417; C10G 45/68
(Continued)

(56) References Cited

U.S. PATENT DOCUMENTS 2,430,516 A * 11/1947 Lien ......................... C07C 2/00
 423/483
4,056,575 A 11/1977 Gregory et al.
(Continued)

FOREIGN PATENT DOCUMENTS

WO   1996011175 A1   4/1996
WO   2004013095 A2   2/2004
(Continued)

OTHER PUBLICATIONS

Haynes, W. M. "CRC Handbook of Chemistry and Physics", 95th Edition (Internet Version 2015); pp. 34 and 298. (Year: 2015).*
(Continued)

*Primary Examiner* — Youngsul Jeong
(74) *Attorney, Agent, or Firm* — Cantor Colburn LLP (57) ABSTRACT

A process for producing cumene and/or ethylbenzene from a mixed hydrocarbon feedstream comprising subjecting C6 cut separated from said mixed hydrocarbon feedstream to aromatization to provide an aromatization product stream and subjecting the thus obtained aromatization product stream to alkylation to produce an alkylated aromatic stream.

14 Claims, 3 Drawing Sheets

(51) Int. Cl.
  *C10G 45/68* (2006.01)
  *C10G 29/20* (2006.01)
  *C10G 69/12* (2006.01)
  *C10G 45/70* (2006.01)
  *C07C 15/04* (2006.01)
  *C07C 15/073* (2006.01)
  *C07C 15/085* (2006.01)

(52) U.S. Cl.
  CPC .......... *C07C 15/073* (2013.01); *C07C 15/085* (2013.01); *C10G 29/205* (2013.01); *C10G 45/68* (2013.01); *C10G 45/70* (2013.01); *C10G 69/123* (2013.01); *C07C 2529/18* (2013.01); *C07C 2529/40* (2013.01); *C07C 2529/44* (2013.01); *C07C 2529/70* (2013.01)

(58) Field of Classification Search
  USPC ............. 585/323, 407, 413; 208/62, 79, 133
  See application file for complete search history.

(56) References Cited

U.S. PATENT DOCUMENTS

| | | | |
|---|---|---|---|
| 4,157,356 | A | 6/1979 | Bulford et al. |
| 4,180,689 | A | 12/1979 | Davies et al. |
| 4,456,527 | A | 6/1984 | Buss et al. |
| 4,594,145 | A * | 6/1986 | Roarty ................... C10G 59/06 208/133 |
| 4,867,864 | A * | 9/1989 | Dessau ................ C10G 35/095 208/138 |
| 4,975,179 | A * | 12/1990 | Harandi ................. C10G 63/00 208/133 |
| 5,043,506 | A | 8/1991 | Crossland |
| 6,002,057 | A | 12/1999 | Hendriksen et al. |
| 6,008,422 | A | 12/1999 | Schulz et al. |
| 6,063,976 | A | 5/2000 | Hendriksen et al. |
| 6,177,600 | B1 | 1/2001 | Netzer |
| 7,405,336 | B2 | 7/2008 | Kelly et al. |
| 7,902,413 | B2 | 3/2011 | Stevenson et al. |
| 8,242,320 | B2 | 8/2012 | Schmidt |
| 2006/0247479 | A1 | 11/2006 | Barchha et al. |
| 2008/0194890 | A1 | 8/2008 | Brown |
| 2008/0255398 | A1* | 10/2008 | Stevenson ................ B01J 29/04 585/407 |
| 2008/0293990 | A1 | 11/2008 | Stevenson et al. |
| 2009/0137855 | A1* | 5/2009 | Clark ....................... C07C 2/66 585/435 |
| 2012/0330076 | A1 | 12/2012 | Smith et al. |
| 2013/0231511 | A1* | 9/2013 | Wu ........................... B01J 38/46 585/407 |
| 2013/0237731 | A1 | 9/2013 | Majumder et al. |
| 2013/0237733 | A1 | 9/2013 | Majumder et al. |
| 2014/0094632 | A1* | 4/2014 | Shecterle ................... B01J 8/00 585/400 |

FOREIGN PATENT DOCUMENTS

| | | |
|---|---|---|
| WO | 2005085157 A1 | 9/2005 |
| WO | 2008124852 A2 | 10/2008 |
| WO | 2008127538 A1 | 10/2008 |
| WO | 2013119318 A1 | 8/2013 |

OTHER PUBLICATIONS

"Catalytic Reforming" (2006); pp. 238-248. (Year: 2006).*
Alexander Coker, ChemSystems PERP Program, Phenol/Acetone/Cumene, PERP 09-10-4, Feb. 2012, 201 Pages.
Alfke et al. (2007) Oil Refining, Ullmann's Encyclopedia of Industrial Chemistry; 56 Pages.
Cesar, M. Process Economics Program Report 219, Cumene, Menlo Park, California 94025, Aug. 1999, 165 Pages.
Encyclopaedia of Hydrocarbons (2006) vol. II, Chapter 10.6, Aromatics, p. 591-614.
European Search Report for European Application No. 15174335; Date of Completion: Dec. 3, 2015; 2 Pages.
Hwang, et al., "Cumene—Kirk Othmer Encyclopedia of Chemical Technology", 2010, pp. 1-10.
International Patent No. 1996011175(A1); Date of Publication: Apr. 18, 1996; Machine Translation; 8 Pages.
International Search Report for International Application No. PCT/EP2016/064571; Date of Completion: Aug. 29, 2016; dated Sep. 2, 2016; 6 Pages.
Nagamori et al, "Coverting light hydrocarbons containing olefins to aromatics (Alpha Process)," Microporous and Mesopourous Materials 21 (1998) 439-445.
Vora et al., "Alkylation—Kirk Othmer Encyclopedia of Chemical Technology", 2003, vol. 2, 35 pages.
Written Opinion for International Application No. PCT/EP2016/064571; International Filing Date: Jun. 23, 2016; Aug. 29, 2016; dated Sep. 2, 2016; 6 Pages.

* cited by examiner

PROCESS FOR PRODUCING CUMENE AND/OR ETHYLBENZENE FROM A MIXED HYDROCARBON FEEDSTREAM

CROSS REFERENCE TO RELATED APPLICATIONS

This application is a 371 of International Application No. PCT/EP2016/064571, filed Jun. 23, 2016, which claims priority to European Application No. 15174335.8, filed Jun. 29, 2015, both of which are incorporated herein by reference in their entirety.

The present invention relates to a process for producing cumene and/or ethylbenzene from a mixed hydrocarbon feedstream comprising subjecting a C6 cut separated from said mixed hydrocarbon feedstream to aromatization to provide an aromatization product stream and subjecting the thus obtained aromatization product stream to alkylation to produce an alkylated aromatic stream.

The commercial production of the benzene derivatives ethylbenzene or cumene comprises the alkylation of benzene using ethylene or propylene as alkylation agent; see e.g. Hwang and Chen (2010) Cumene Kirk-Othmer Encyclopedia of Chemical Technology 1-10. Direct alkylation of a mixed C6 hydrocarbon feedstream is not a viable method to produce high-purity ethylbenzene or cumene since in such a process many undesired by-products are produced which are difficult to separate from the desired aromatic alkylation products; see e.g. U.S. Pat. No. 6,177,600. Therefore, a mixed hydrocarbon feedstream such as reformate or C6 cut conventionally needs to be subjected to aromatic extraction, such as liquid extraction or extractive distillation, to remove the benzene co-boilers in order to provide a sufficiently purified benzene stream. A drawback of such a process for producing benzene is that aromatic extraction methods are expensive and time consuming.

Furthermore, the alkylation of benzene to ethylbenzene or cumene requires a tight control of the reaction exotherm. For instance, the alkylation of benzene with propylene is an exothermic reaction with a reaction heat of $-4.3 \times 10^4$ Btu/lbmol. Conventionally, benzene is used in excess of the stoichiometric amount. A high molar ratio acts as a heat sink and controls the exothermic temperature rise in the reactor, thus reducing n-propylbenzene formation which is promoted at high temperature. In addition, the excess benzene reduce the amount of polyalkylated by-products formed during the reaction. Diisopropylbenzene (DIPB) and triisopropylbezene (TIPB) are the major polyalkylated by-products formed; DIPB is formed by the reaction of cumene with propylene and TIPB is produced by the reaction of DIPB with propylene. The excess benzene is recovered in a distillation column and recycled to the reactor, which reflects in the cost of separating the excess benzene. The use of interstage coolers for heat removal from the alkylation reaction zone by indirect heat exchange provides a conventional alternative to direct heat exchange for reducing the temperature differential across the alkylation reaction zone. In addition, the reaction temperature may be conventionally controlled by the staged addition of propylene reactant also serving as an interstage reactor quench.

Another method to control the temperature rise in the reactor is to recycle a portion of the alkylation reactor effluent. Thus, while effluent recycle is conventionally used to limit the maximum alkylation reaction zone temperature, this benefit is achieved at the expense of obtaining an alkylation effluent comprising cumene at well below the equilibrium level of a cumene/DIPB/TIPB mixture under the alkylation reaction zone conditions.

U.S. Pat. No. 4,975,179 A describes a fixed bed process for the alkylation of reformate comprising C6-hydrocarbons to produce high octane gasoline, comprising; (a) separating a naphtha feedstream by fractionation into a lower boiling fraction comprising iso-C6 aliphatic hydrocarbon components and a reformer feedstock fraction comprising higher boiling C6+ aliphatic hydrocarbon components; (b) reforming the reformer feedstock fraction comprising the higher boiling C6+ aliphatic components in contact with reforming catalyst and under reforming conditions to produce a reformate containing benzene and C7+ hydrocarbons; (c) separating said reformate into a C6− hydrocarbon stream containing benzene and paraffins and a C7+ hydrocarbon stream; (d) introducing said C6− hydrocarbon stream and alkylating agent into an alkylating zone in contact with acidic metallosilicate catalyst under alkylating conditions whereby benzene is alkylated to produce high octane gasoline containing C7+ aromatic hydrocarbons. In the process according to U.S. Pat. No. 4,975,179 A, only the n-hexane is subjected to catalytic reforming. the iso-C6 aliphatic hydrocarbon component is discarded and not subjected to the catalytic reforming process step.

It was an object of the present invention to provide an improved process for producing alkylated aromatics from a mixed hydrocarbon feedstream.

The solution to the above problem is achieved by providing the embodiments as described herein below and as characterized in the claims. Accordingly, the present invention provides a process for producing alkylated aromatics comprising:

(a) subjecting a mixed hydrocarbon feedstream to a separation to provide a C6 cut;
(b) subjecting C6 cut to aromatization to provide an aromatization product stream;
(c) subjecting the thus obtained aromatization product stream to alkylation to produce an alkylated aromatic stream.

In the context of the present invention, it was surprisingly found that by subjecting the aromatization product stream to alkylation, the alkylation reaction exotherm can be much more easily controlled when compared to conventional aromatic alkylation processes, wherein a purified benzene stream is subjected to alkylation. This allows a much simpler design of the alkylation reactor, for instance a reactor comprising one reactor bed instead of a series of reactor beds with the need of intermittent quenching to control the reaction exotherm. Moreover, the process of the present invention leads to a reduced production of undesired side-products.

The term "aromatic hydrocarbons" or "aromatics" is very well known in the art. Accordingly, the term "aromatic hydrocarbon" relates to cyclically conjugated hydrocarbon with a stability (due to delocalization) that is significantly greater than that of a hypothetical localized structure (e.g. Kekulé structure). The most common method for determining aromaticity of a given hydrocarbon is the observation of diatropicity in the 1H NMR spectrum, for example the presence of chemical shifts in the range of from 7.2 to 7.3 ppm for benzene ring protons.

As used herein, the term "C # hydrocarbons", or "C #", wherein "#" is a positive integer, is meant to describe all hydrocarbons having # carbon atoms. Moreover, the term "C #+ hydrocarbons" is meant to describe all hydrocarbon molecules having # or more carbon atoms. Accordingly, the term "C9+ hydrocarbons" is meant to describe a mixture of hydrocarbons having 9 or more carbon atoms. The term "C9+ alkanes" accordingly relates to alkanes having 9 or more carbon atoms.

In the process of the present invention, any mixed hydrocarbon composition that comprises C6 hydrocarbons and that is suitable to be subjected to aromatization can be used as a feedstream. Such a suitable feedstream may be selected from the group consisting of reformate, C6 cut, straight run naphtha, hydrocracked gasoline, light coker naphtha, coke oven light oil and FCC gasoline, or mixtures thereof.

Preferably, the feedstream comprises reformate.

The process of the present invention comprises subjecting a mixed hydrocarbon feedstream to a separation to provide a C6 cut. As used herein, the term "C6 cut" relates to a hydrocarbon fraction comprising at least 60 wt-% C6 hydrocarbons, preferably at least 70 wt-% C6 hydrocarbons, more preferably at least 80 wt-% C6 hydrocarbons, particularly preferably at least 90 wt-% C6 hydrocarbons, more particularly preferably at least 95 wt-% C6 hydrocarbons, and most preferably at least 99 wt-% C6 hydrocarbons. Accordingly, the C6 cut comprises a mixture of C6 hydrocarbons selected from the group consisting of n-alkanes, isoalkanes, naphthenes and aromatics. Preferably, the C6 cut comprises iso-hexane. Preferably, the separation to provide a C6 cut does not involve aromatic extraction, such as liquid extraction or extractive distillation. Preferably, the separation to provide a C6 cut involves distillation. The skilled person is capable of selecting the suitable distillation conditions to provide a C6 cut as defined herein. Preferably, the distillation conditions are suitable to provide a C6 cut having a boiling point range of 45-90° C., more preferably of 47-87° C., particularly preferably of 48-85° C. and most preferably 49-81° C. Accordingly, it is preferred that the process of the present invention comprises the separation of the mixed hydrocarbon feedstream to provide a C6 cut that involves distillation and wherein the distillation conditions are suitable to provide a C6 cut having a boiling point range of 45-90° C. A C6 cut from reformate can vary a lot in composition. Preferably, the benzene content of the C6 cut varies between 10-50 wt-% with the remainder being mainly paraffins, of which iso-paraffins are much more dominant. The naphthene content is rather low (preferably less than 10 wt-%), particularly when the feedstream comprises reformate since refinery reformers dehydrogenate the naphthenic species almost completely. The hydrocarbons comprised in the mixed hydrocarbon feedstream and which are not comprised in the C6 cut, such as the C7+ cut, may be subjected to further chemical processing or separation or may be used as such. Preferably, the C7+ cut is added to the gasoline blending pool.

The process of the present invention comprises aromatization of the C6 cut to provide an aromatization product stream.

Preferably, the aromatization comprises contacting the C6 cut with an aromatization catalyst under aromatization conditions. The process conditions useful for aromatization, also described herein as "aromatization conditions", can be easily determined by the person skilled in the art; see Encyclopaedia of Hydrocarbons (2006) Vol II, Chapter 10.6, p. 591-614.

The term "aromatization" is used herein in its generally accepted sense and thus may be defined as a process to convert aliphatic hydrocarbons to aromatic hydrocarbons. There are many aromatization technologies described in the prior art using C3-C8 aliphatic hydrocarbons as raw material; see e.g. U.S. Pat. Nos. 4,056,575; 4,157,356; 4,180,689; 4,456,527; Micropor. Mesopor. Mater 21, 439; WO 2004/013095 A2 and WO 2005/085157 A1. Accordingly, the aromatization catalyst may comprise a zeolite, preferably selected from the group consisting of ZSM-5 and zeolite L, and may further comprise one or more elements selected from the group consisting of Ga, Zn, and Ge and a hydrogenation metal which is preferably selected from the group consisting of Pt, Pd, In, Rh, and Ru.

Preferably, the silicon to aluminum atomic ratio (Si:Al) of the zeolite is greater than 2, more preferably in the range from 10 to 200 and even more preferably in the range from 20 to 100. Preferably, the zeolite a medium pore zeolite. Preferably, the average pore size of the zeolite is in the range from 5 to 7 angstroms. Preferably, the zeolite is selected from the group consisting of ZSM-5 and zeolite L. Most preferably, the zeolite is ZSM-5. Preferably, the zeolite comprises Ge as a framework element. Preferably, the germanium content of the zeolite having Ge as framework element is in the range from 0.05% to 10% by weight, more preferably from 2% to 8% by weight and even more preferably in the range of from 0.05% to 3%.

Preferably, the hydrogenation metal is present in the range of from 0.2 wt-% to 2 wt-%, and more preferably in the range of from 0.2 wt-% to 1.5 wt-%. Preferably, the noble metal is platinum, palladium, indium, rhodium or ruthenium and more preferably platinum.

Preferably, the aromatization catalyst used in the process of the present invention is non-acidic. As used herein, the term "non-acidic zeolite" relates to a zeolite that comprises less than 0.2 wt-% Al, preferably less than 0.1 wt-% Al and most preferably less than 0.05 wt-% Al. or which has been subjected to base-exchange. Accordingly, the zeolite either comprises substantially no aluminium sites in the zeolite framework or the aluminium sites in the zeolite framework are exchanged with base cations. The zeolite is preferably base-exchanged with an alkali metal or alkaline earth metals such as cesium, potassium, sodium, rubidium, barium, calcium, magnesium and mixtures thereof, most preferably cesium. Base-exchange may take place during synthesis of the zeolite with an alkali metal or alkaline earth metal being added as a component of the reaction mixture or may take place with a crystalline zeolite before or after deposition of a noble metal. The zeolite is base-exchanged to the extent that most or all of the cations associated with aluminum are alkali metal or alkaline earth metal. An example of a monovalent base:aluminum molar ratio in the zeolite after base exchange is at least about 0.9.

The aromatization catalyst preferably is a non-acidic zeolite comprising Ge as a framework element.

The aromatization catalyst preferably is non-acidic by base-exchange and/or further comprises a hydrogenation metal, preferably Pt.

Preferably, the zeolite comprised in the aromatization catalyst is ZSM-5. More preferably, the aromatization catalyst is selected from the group consisting of ZSM-5, Ga/ZSM-5, Zn/ZSM-5 and Pt/GeZSM-5. More preferably, the catalyst is Pt/GeZSM-5. As used herein, the term "Pt/GeZSM-5" is meant to describe a platinum-modified ZSM-5 zeolite comprising Ge as a framework element. The Pt/GeZSM-5 preferably comprises from 0.2 wt-% to 2 wt-% Pt, more preferably from 0.2 wt-% to 1.5 wt-% Pt. Even more preferably, the aromatization catalyst comprises a non-acidic Pt/GeZSM-5 zeolite. Most preferably, the catalyst is Pt/GeZSM-5 that is based-exchanged with Cs as described in WO 2008/127538 A1.

In the context of the present invention, it was surprisingly found that the benzene yield of a process for the aromatization of a C6 cut can be increased by specifically selecting Pt/GeZSM-5 that is based-exchanged with Cs as the aromatization catalyst.

The aromatization conditions preferably comprise a temperature of 400-600° C., preferably 450-550° C. a pressure of 50-1000 kPa gauge, preferably 75-500 kPa gauge, and a Weight Hourly Space Velocity (WHSV) of 0.1-20 h$^{-1}$, preferably of 0.4-4 h$^{-1}$.

Preferably, the aromatization comprises contacting the C6 cut with an aromatization catalyst under aromatization conditions, wherein the aromatization catalyst comprises a zeolite selected from the group consisting of ZSM-5 and zeolite L, optionally further comprising one or more elements selected from the group consisting of Ga, Zn, Ge and Pt and wherein the aromatization conditions comprise a temperature of 400-600° C., preferably 450-550° C. a pressure of 50-1000 kPa gauge, preferably 75-500 kPa gauge, and a Weight Hourly Space Velocity (WHSV) of 0.1-20 h$^{-1}$, preferably of 0.4-4 h$^{-1}$.

It may be required to subject the mixed hydrocarbon feedstream and/or the C6 cut to desulphurization to prevent deactivation of the aromatization catalyst. This is particularly important in case a feedstream is selected that is relatively rich in sulfur compounds such as straight run naphtha, light coker naphtha, coke oven light oil or mixtures thereof. Moreover, particular aromatization catalyst are particularly sensitive for deactivation by sulfur compounds such as zeolite L-based catalysts. Means and methods suitable for desulfurization of hydrocarbon streams are well known in the art and include hydrodesulfurization. Such a hydrodesulfurization process is performed in a "HDS unit" or "hydrotreater"; see Alfke et al. (2007) Oil Refining, Ullmann's Encyclopedia of Industrial Chemistry. Generally, the hydrodesulfurization reaction takes place in a fixed-bed reactor at elevated temperatures of 200-425° C., preferably of 300-400° C. and elevated pressures of 1-20 MPa gauge, preferably 1-13 MPa gauge in the presence of a catalyst comprising elements selected from the group consisting of Ni, Mo, Co, W and Pt, with or without promoters, supported on alumina, wherein the catalyst is in a sulfide form. Preferably, the C6 cut that is contacted with the aromatization catalyst comprises less than 5 wt-ppm sulfur, more preferably less than 1 wt-ppm sulfur. In case zeolite L-based aromatization catalysts is selected, the sulfur content of the C6 cut that is contacted with the aromatization catalyst preferably comprises less than 50 wt-ppb sulfur, more preferably less than 10 wt-ppb sulfur. In case a non-acidic zeolite comprising Ge as a framework element is selected as aromatization catalyst, sulfur content of the C6 cut that is contacted with the aromatization catalyst preferably comprises less than 50 wt-ppm of sulfur, more preferably less than 10 wt-ppm of sulfur and most preferably less than 2 wt-ppm of sulfur. Accordingly, an advantage of selecting a non-acidic zeolite comprising Ge as a framework element as aromatization catalyst is that this catalyst is more resistant to sulfur impurities in the feed.

As used herein, the term "aromatization product stream" relates to the product stream obtained when subjecting a C6 cut to aromatization. Hence, the aromatization product stream obtained by aromatization of the C6 cut is directly subjected to alkylation using ethylene or propylene as alkylation agent, without subjecting said aromatization product stream to any kind of separation.

In one embodiment, the process of the present invention involves subjecting the aromatization product stream to separation to provide a C6 fraction, wherein the thus obtained C6 fraction is subsequently subjected to alkylation to produce the alkylated aromatic stream. Preferably, the separation of the aromatization product stream to provide the C6 fraction involves distillation and wherein the distillation conditions are suitable to provide a C6 fraction having a boiling point range of 49-80° C. Preferably, the separation to provide a C6 fraction involves distillation. The skilled person is capable of selecting the suitable distillation conditions to provide a C6 fraction as defined herein. Preferably, the distillation conditions are suitable to provide a C6 fraction having a boiling point range of 49-80° C., more preferably of 51-71° C., particularly preferably of 53-68° C. and most preferably 54-64° C. The hydrocarbons comprised in the aromatization product stream and which are not comprised in the C6 fraction, such as the C5− hydrocarbons and or the C7+ hydrocarbons, may be subjected to further chemical processing or separation or may be used as such. Preferably, the C6 fraction comprises 15-70 wt-% benzene, preferably 40-50 wt-% benzene. Preferably, the C6 fraction that is subjected to alkylation comprises C6 non-aromatics. Preferably, the C6 fraction comprises 30-85 wt-% hexane, preferably 50-60 wt-% hexane. More preferably, the C6 fraction comprises 15-60 wt-% benzene and 40-85 wt-% hexane, preferably 40-50 wt-% benzene and 50-60 wt-% hexane. Preferably, the hexane comprised in the C6 fraction is one or more selected from the group consisting of isohexane and normal-hexane.

The process of the present invention further comprises subjecting the C6 fraction to alkylation to produce an alkylated aromatic stream.

Accordingly, the process of the present invention involves alkylation, which comprises contacting the benzene comprised in the C6 fraction with an alkylation agent in the presence of an alkylation catalyst under alkylation conditions. The process conditions useful alkylation, also described herein as "alkylation conditions", can be easily determined by the person skilled in the art; see e.g. Vora et al. (2003) Alkylation Kirk-Othmer Encyclopedia of Chemical Technology and Hwang and Chen (2010) loc. cit. The process conditions used for alkylation generally includes a process temperature of 100-300° C., a pressure of 0.5-10 MPa, a weight hourly space velocity of 0.5-20 h$^{-1}$ and benzene/alkylation agent molar ratio of 3-10. The benzene alkylation process step uses an acidic catalyst which may be a solid phosphoric acid catalyst (phosphoric acid supported on alumina) or an aluminum chloride complex as the catalyst or an acidic zeolite-based catalyst. Preferably, the zeolite comprised in the alkylation catalyst has a pore size of 6-8 Å. The optimal process conditions depend on the alkylation agent. For instance, when selecting propylene as the alkylation agent the process conditions are somewhat milder when compared to selecting ethylene as the alkylation agent.

The alkylation preferably comprises contacting the benzene comprised in the C6 fraction in the presence of ethylene with an alkylation catalyst under alkylation conditions to produce ethylbenzene, wherein said alkylation catalyst comprises beta zeolite, zeolite Y, ZSM-12, MCM-22, ZSM-5 and mordenite and wherein said alkylation conditions comprise a temperature of 120-250° C. preferably of 150-230° C. a pressure of 1000-5000 kPa, preferably of 2500-3500 kPa, a Weight Hourly Space Velocity (WHSV) of 0.5-20 h$^{-1}$, preferably of 1-10 h$^{-1}$ and a benzene/ethylene molar ratio of 1-8, preferably of 1-4.

Alternatively, the alkylation preferably comprises contacting the benzene comprised in the C6 fraction in the presence of propylene with an alkylation catalyst under alkylation conditions to produce cumene, wherein said alkylation catalyst comprises a zeolite selected from the group consisting of beta zeolite, zeolite Y, ZSM-12, MCM-22, ZSM-5 and mordenite and wherein said alkylation conditions comprise a temperature of 120-250° C. preferably of 150-230° C. a pressure of 1000-5000 kPa, preferably of 2500-3500 kPa, a Weight Hourly Space Velocity (WHSV) of 0.5-20 h$^{-1}$, preferably of 1-10 h$^{-1}$ and a benzene/propylene molar ratio of 1-8, preferably of 1-4.

Preferably, the alkylated aromatic stream is subjected to a separation to provide a monoalkylated aromatic product stream and stream comprising polyalkylated aromatic product stream and wherein said polyalkylated aromatic products are subjected to transalkylation. Suitable transalkylation processes to convert a feed comprising polyalkylated aromatic hydrocarbons to monoalkylated aromatic hydrocarbons are well known in the art.

It is noted that the invention relates to all possible combinations of features described herein, particularly features recited in the claims.

It is further noted that the term "comprising" does not exclude the presence of other elements. However, it is also to be understood that a description on a product comprising certain components also discloses a product consisting of these components. Similarly, it is also to be understood that a description on a process comprising certain steps also discloses a process consisting of these steps.

The present invention will now be more fully described by the following non-limiting Examples.

Figure 1:
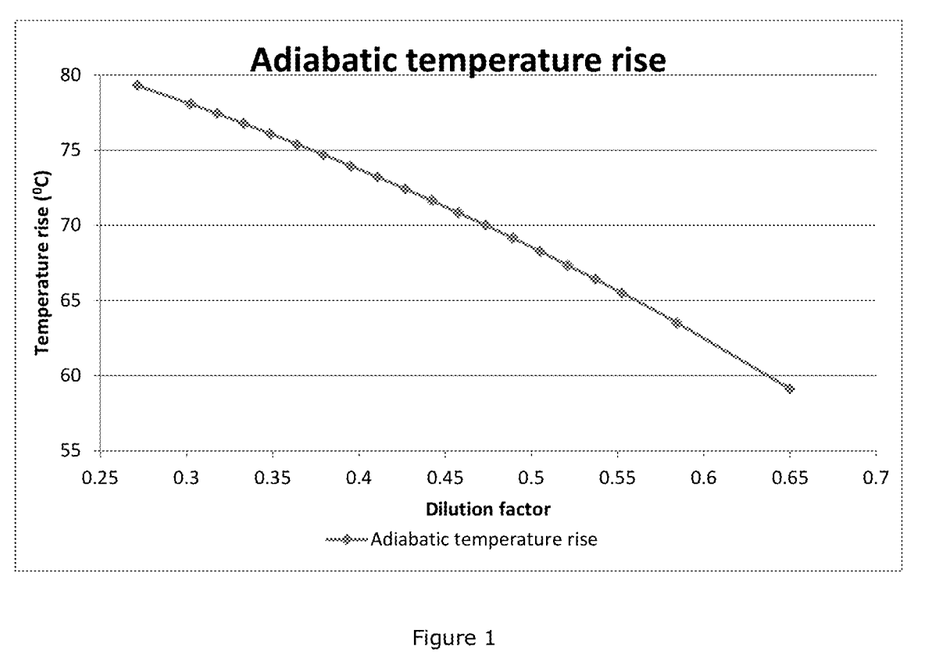

FIG. 1 shows the adiabatic temperature rise plotted against the dilution factor for diluted feedstock (Process conditions: pressure=30 bar, benzene/olefins molar ratio=2.5, Inlet temp=180° C.). The dilution factor as defined in the present invention is the weight fraction of the non-aromatics present in the diluted feedstock.

Figure 2:
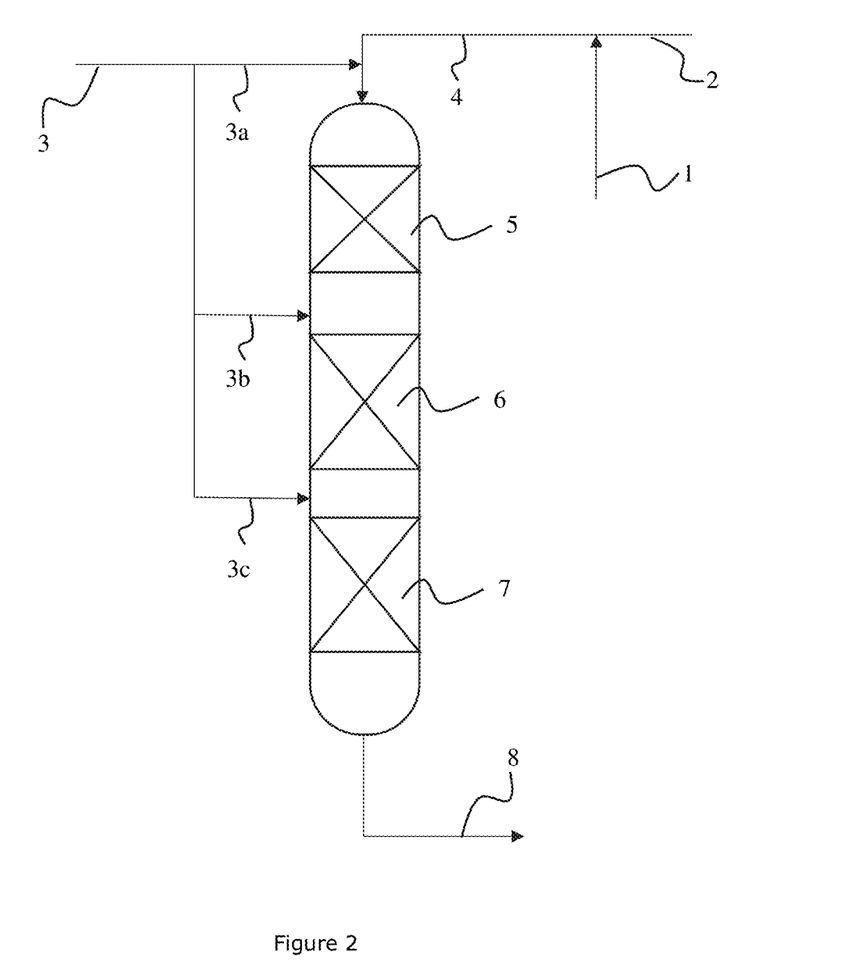

FIG. 2 shows a reactor configuration in which the reactor consists of three beds 5, 6, and 7 in series. Fresh benzene stream 1 is mixed with the benzene recycle stream 2 from the benzene column in the downstream separation process. The propylene feed 3 is split and fed to each reactor stage. The fresh benzene stream 1 and propylene stream 3 provides the benzene to propylene stoichiometric ratio of 1:1. The mixed benzene stream 4 and propylene stream 3a is fed to the inlet of the first reactor bed 5. The effluent from 5 is mixed with stream 3b and fed to reactor bed 6. The sequence applies for reactor bed 7, i.e., the effluent from reactor bed 6 is mixed with stream 3c and fed to reactor bed 7. The product stream 8 is a mix of alkylated products such as cumene, diisopropylbenzene, triisopropylbezene, unreacted benzene, propane, n-hexane, and iso-hexanes.

Figure 3:
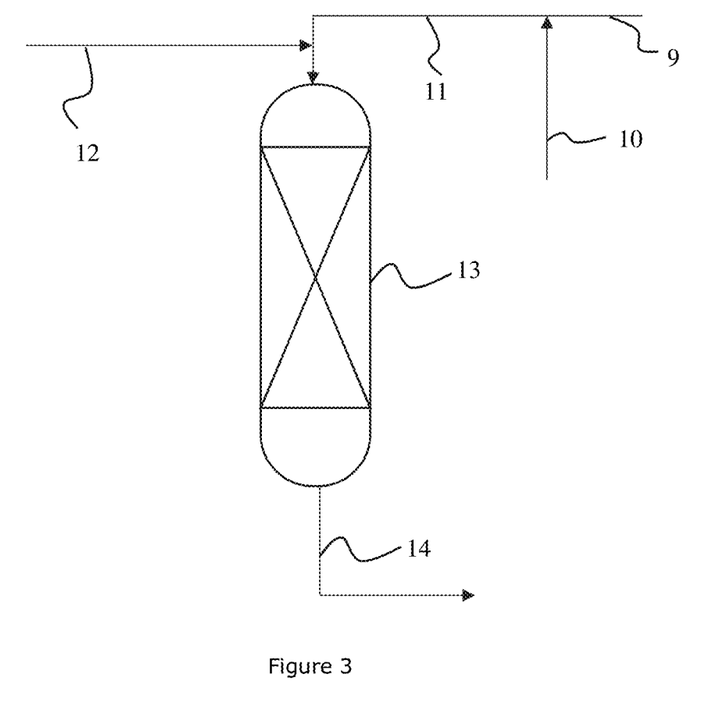

FIG. 3 shows a simple reactor configuration with a single bed 13. Fresh benzene stream 10 is mixed the benzene recycle stream 9 from the benzene column in the separation section of the alkylation process. The fresh benzene and the propylene stream 12 provides the benzene to propylene stoichiometric ratio of 1:1. The mixed benzene stream 11 is fed with the propylene stream into the reactor. The product stream 14 is a mix of alkylated products such as cumene, diisopropylbenzene, triisopropylbezene, unreacted benzene, propane, n-hexane, and iso-hexanes. Stream 14 is subjected to separation in the downstream process.

EXAMPLE 1

Cs-Exchanged Pt/GeZSM-5 Aromatization Catalyst

This catalyst consists of Pt dispersed on a basic ZSM-5 zeolite containing framework germanium (1% Pt/CsGeZSM-5). This catalyst may be prepared as described in U.S. Pat. No. 7,902,413 or US 2008/0293990 A1.

Accordingly, Ge-ZSM-5 Zeolite may be prepared as follows: Solution #1 is made by diluting 15.84 g of 50 wt-% NaOH solution with 131.25 g of deionized (DI) water and subsequently dissolving 7.11 g of germanium dioxide. Solution #2 is made by diluting 3.84 g sodium aluminate solution (23.6 wt-% alumina and 19.4 wt-% sodium oxide) with 153.9 g DI water. Solution #1 is added to 150 g Ludox AS-40 (40 wt-% silica in a colloidal state) and vigorously stirred for 10 minutes to obtain a homogeneous mixture. Solution #2 is stirred into this mixture. After 15 minutes of vigorous agitation, 105.42 g of tetra-n-propyl ammonium hydroxide (TPAOH) is added and the mixture is stirred for 60 minutes. Finally, 23.32 g of glacial acetic acid is added to the gel to adjust the pH of the mixture to about 9. This mixture is loaded into a 1 L stainless steel autoclave and heated at 160° C. for 36 hours with stirring. Subsequently, the solids obtained are filtered from the mother liquor and washed with DI water. The solid is calcined at 550° C. for 6 hours in an oven with air flow. The MFI structure of the solid can be confirmed by measuring the powder X-Ray diffraction pattern.

8 grams of GeZSM-5 prepared as described above are washed with 200 ml of aqueous $CsNO_3$ (0.5M) then filtered. The filtrate is then rewashed 3 more times with 0.5M $CsNO_3$ and rinsed with distilled $H_2O$ on the final filtering. The zeolite powder is then calcined for 3 hours at 280° C. in air. Incipient wetness impregnation is carried out by adding drop wise a solution of 0.069 g $Pt(NH_2)_4(NO_3)_2$ dissolved in 1.343 g of deionized water to 3.508 grams of the Cs-exchanged Ge ZSM-5. The material is dried for 1 hour in a 110° C. drying oven then calcined at 280° C. for 3 hours. A representative elemental analysis gives 39.92 wt-% Si, 0.69 wt-% Al, 4.14 wt-% Ge, 5.03 wt-% Cs, and 0.90 wt-% Pt. The catalyst powder is typically pressed and sized to 20-40 mesh.

EXAMPLE 2

Aromatization of C6 Heart Cut

The experimental data as provided herein were obtained by modelling the product slates of an aromatization unit fed with reformate C6 heart cut feed. In this aromatization isohexanes ("iso-C6") and normal hexanes ("n-C6") are transformed into benzene, naphthenic species are dehydrogenated into benzene.

Reaction tests are carried out using a 0.31 inch ID reactor tube containing a catalyst bed comprising 1 to 4.32 cm$^3$ of the aromatization catalysts as described above in Examples 1 and 2. The bed is diluted to a total of 8 cm$^3$ with inert silicon carbide to maintain constant length. Liquid n hexane is vaporized and passed over the catalyst bed at temperatures ranging from 500 to 540° C., pressures between 103 kPa absolute (15 psia) and 310 kPa absolute (45 psia), and liquid hourly space velocities ranging from 1 to 8 hr$^{-1}$. Products are analysed by on-line gas chromatography. Further experiments are carried out in two adiabatic pilot reactors connected in series, where n-hexane or light naphtha is vaporized and passed over a bed containing 80 g of catalyst per reactor, at an inlet temperature of 540° C., outlet temperatures at or above 450° C., and pressures ranging from 241 kPa absolute (35 psia) to 62 kPa absolute (9 psia). For these experiments, products are analysed both by on-line gas chromatography and by off-line analysis of collected liquid samples.

The experimental data as provided herein were obtained by modelling the product slates of an aromatization unit fed with reformate C6 heart cut feed. In this example three cases are considered, i.e. a low, medium and high benzene concentration in the c6 heart cut feed. One-pass experiments allow the estimation of what conversions would be obtained in a complete process using partial recycle of unconverted hexanes; the predicted conversions are shown in Table 1:

TABLE 1

Conversions for C6 hydrocarbons obtained in the aromatization experiment described above.

| | % |
|---|---|
| Benzene | 0 |
| iso-C6 | 25 |
| n-C6 | 75 |
| cyclo-C6 | 100 |

A C6 cut from reformate may vary in composition. Roughly, the benzene content varies between 10-50 wt-% with the remainder being mainly paraffins, of which iso-paraffins are much more dominant. The naphthene content (mainly cyclohexane "cyclo-C6") typically is below 10 wt-% since refinery reformers dehydrogenate the naphthenic species almost completely.

TABLE 2

Three feed scenarios modelled in this example
C6 heart cut feed composition (wt-%)

| | LOW | MEDIUM | HIGH |
|---|---|---|---|
| Benzene | 17 | 35 | 50 |
| iso-C6 | 56 | 44 | 34 |
| n-C6 | 22 | 17 | 13 |
| cyclo-C6 | 5 | 4 | 3 |
| Sum | 100 | 100 | 100 |

Based on the examples explained above and given the obtained conversions explained in table 1 the following product slates are modelled for the three feed scenario's described in table 2.

The tables below indicate the estimated effluent composition of an aromatization unit with Cs-exchanged Pt/GeZSM-5 aromatization catalyst.

TABLE 3

Aromatization effluent composition in the aromatization unit with using Cs-exchanged Pt/GeZSM-5 aromatization catalyst as described in Example 1. All numbers in wt-%.

Aromatization effluent composition

| | LOW | MEDIUM | HIGH |
|---|---|---|---|
| Benzene | 46 | 58 | 70 |
| iso-C6 | 42 | 33 | 25 |
| n-C6 | 6 | 4 | 3 |
| cyclo-C6 | 0 | 0 | 0 |
| Hydrogen & Light gases (C1-C4) | 6 | 5 | 2 |

Accordingly, it was found that n-C6, cyclo-C6 and the iso-C6 comprised in the C6 heart cut are converted into benzene when using a Cs-exchanged Pt/GeZSM-5 aromatization catalyst.

EXAMPLE 3

Aromatic Alkylation

In this example, the aromatic alkylation is carried with a model feed which is a diluted C6 stream containing 50 wt-% of benzene and the remaining diluted with iso-hexanes and n-hexane. The feed composition as used in this Example was 50 wt-% benzene, 34 wt-% iso-hexanes, 13 wt-% n-hexane, and 3 wt-% cyclohexane. The alkylation agent (olefin) is a mixture of ethylene and propylene at a weight ratio of 3:1.

The reaction was carried out using a 3.5 mm ID reactor, which contains 1.35 ml catalyst volume available in an isothermal zone of 14 cm. This corresponds to approximately 0.1 ml catalyst/cm height. The catalyst is a BETA zeolite catalyst with Si/Al molar ratio of about 38. The undiluted zeolite is ~0.65 g/ml in the reactor. The benzene to olefin molar ratio is 4, WHSV of 2 hr-1, reaction temperature of 200° C., and pressure of 25 bars. The product slate shows complete conversion of ethylene and propylene and 22% conversion of benzene. The combined selectivity of ethylbenzene and cumene is 87 wt-% while the polyalkylated byproducts (polyethylatedbenzene and ploypropylated benzene) is 13 wt-%. The amount of diluents in the product slates shows negligible conversion (<1%) which indicates that the n-hexane and iso-hexane acts as inerts in the alkylation reactor.

EXAMPLE 4

Aromatic Alkylation Modelling

The data as provided in this example were obtained by modelling the alkylation of the C6 fraction with propylene using an equilibrium reactor model. The feed compositions as used for the modelling experiments are described in Tables 4 and 5, below. The olefin stream contains 70 wt-% propylene and 30 wt-% propane. The reaction is carried out at 180° C. and 30 bar, with a benzene to propylene molar ratio of 2.5. Table 4 shows the result of the temperature rise and product selectivity using a single bed reactor. Table 5 shows the result of the temperature rise and product selectivity using a three staged reactor bed with interstage feeding of propylene. The effect of the diluents on the temperature rise is shown in FIG. 1.

TABLE 4

Adiabatic temperature rise for a single staged reactor configuration

| | C6 fraction | Pure benzene |
|---|---|---|
| Feed (wt-%) | | |
| Benzene | 40 | 100 |
| Iso-hexane | 56 | 0 |
| n-hexane | 4 | 0 |
| ΔT (° C.) | 73 | 109 |
| Selectivity (wt-%) | | |
| Cumene | 86 | 80 |
| DIPB | 12 | 16 |
| TIPB | 2 | 4 |

The term selectivity is defined with respect to propylene as the weight of monoalkylated or polyalkylated product divided by the sum of the weight of monoalkylated and polylaklylated products. For instance, the selectivity of cumene is the weight of cumene divided by the sum of the weight of cumene, DIPB, and TIPB. The results shown in Table 4 compares the exotherm for a diluted feed and pure benzene. A temperature rise of 73° C. indicates that the outlet reactor temperature is about 253° C., which is within the temperature range for alkylation reaction. For a pure benzene feedstock, the temperature rise of 109° C. amounting to an outlet temperature of 289° C. is undesirable for such process. Hence, explains why higher benzene to olefin ratio and/or interstage reactor beds are used to control the temperature rise. It is also expected that high amount of n-propylbenzene will be formed at high temperatures which impacts the purity of cumene. The selectivity of cumene also decreases at high temperatures.

TABLE 5

Adiabatic temperature rise for interstaged reactor configuration

|  | C6 fraction | Pure benzene |
|---|---|---|
| Feed (wt-%) |  |  |
| Benzene | 40 | 100 |
| Iso-hexane | 56 | 0 |
| n-hexane | 4 | 0 |
| ΔT per stage (° C.) | 28-30 | 43-51 |
| Overall ΔT (° C.) | 63 | 89 |
| Selectivity (wt-%) |  |  |
| Cumene | 88 | 86 |
| DIPB | 10 | 12 |
| TIPB | 2 | 2 |

A separate embodiment of the invention also shows that the alkylation can be done in an interstaged reactor with at least three catalyst beds. In Table 5, an improved temperature control is achieved by also feeding propylene at each stage of the catalyst bed. The temperature rise per stage for the diluted feedstock is about 28-30° C., with the outlet temperature from the last reactor stage at 243° C. For the pure benzene feedstock, the reactor outlet temperature also decreased to 269° C. with a temperature rise of about 43-51° C. per stage. The result for the pure benzene feedstock using multiple reactor bed is similar to the result obtained in U.S. Pat. No. 8,242,320 at similar operating conditions. A temperature rise of about 50-61° C. per stage was reported. U.S. Pat. No. 8,242,320 also obtained a temperature rise of about 17-25° C. by recycling a portion of the reactor effluent but at the expense of low selectivity well below equilibrium level.

The present invention affords us the opportunity to carry the alkylation reaction in a simple reactor configuration, which reflects in low capital cost of the equipment, produce high selective products, and obtain an improved temperature control in the alkylation reactor.

The invention claimed is:

1. A process for producing alkylated aromatics comprising:
(a) subjecting a mixed hydrocarbon feedstream to a separation to provide a C6 cut, wherein the C6 cut comprises iso-hexane;
b) subjecting the C6 cut to aromatization to provide an aromatization product stream comprising 25-85 wt-% hexane; and
(c) subjecting the aromatization product stream comprising 25-85 wt-% hexane to alkylation to produce an alkylated aromatic stream.

2. The process according to claim 1, wherein the separation of the mixed hydrocarbon feedstream to provide a C6 cut involves distillation under distillation conditions and wherein the distillation conditions are suitable to provide a C6 cut having a boiling point range of 45-90° C.

3. The process according to claim 1, wherein the aromatization comprises contacting the C6 cut with an aromatization catalyst under aromatization conditions.

4. The process according to claim 3, wherein the aromatization catalyst is a non-acidic zeolite comprising Ge as a framework element.

5. The process according to claim 3, wherein the aromatization catalyst is non-acidic by base-exchange and/or wherein the aromatization catalyst further comprises a hydrogenation metal.

6. The process according to claim 3, wherein the aromatization conditions comprise a temperature of 400-600° C., a pressure of 50-1000 kPa gauge, and a Weight Hourly Space Velocity of 0.1-20 $h^{-1}$.

7. The process according to claim 1, wherein the alkylation comprises contacting the aromatization product stream in the presence of ethylene with an alkylation catalyst under alkylation conditions to produce ethylbenzene, wherein said alkylation catalyst comprises beta zeolite, zeolite Y, ZSM-12, MCM-22, ZSM-5 and mordenite and wherein said alkylation conditions comprise a temperature of 120-250° C., a pressure of 1000-5000 kPa, a Weight Hourly Space Velocity of 0.5-20 $h^{-1}$, and a benzene\ethylene molar ratio of 1-8.

8. The process according to claim 1, wherein the alkylation comprises contacting the aromatization product stream in the presence of propylene with an alkylation catalyst under alkylation conditions to produce cumene, wherein said alkylation catalyst comprises a zeolite selected from the group consisting of beta zeolite, zeolite Y, ZSM-12, MCM-22, ZSM-5 and mordenite and wherein said alkylation conditions comprise a temperature of 120-250° C., a pressure of 1000-5000 kPa, a Weight Hourly Space Velocity of 0.5-20 $h^{-1}$, and a benzene/propylene molar ratio of 1-8.

9. The process according to claim 1, wherein the mixed hydrocarbon feedstream comprises reformate.

10. The process according to claim 7, wherein said alkylation conditions comprise a temperature of 150-230° C., a pressure of 2500-3500 kPa, a Weight Hourly Space Velocity of 1-10 $h^{-1}$ and a benzene/ethylene molar ratio of 1-4.

11. The process according to claim 8, wherein said alkylation conditions comprise a temperature of 150-230° C., a pressure of 2500-3500 kPa, a Weight Hourly Space Velocity of 1-10 $h^{-1}$, and a benzene/propylene molar ratio of 1-4.

12. The process according to claim 1, wherein the C6 cut comprises 34-56 wt-% iso-hexane, based on a total weight of the C6 cut.

13. The process according to claim 1, wherein the aromatization product stream comprises 30-85 wt-% hexane.

14. The process according to claim 1, wherein the aromatization product stream comprises 50-60 wt-% hexane.

* * * * *